US008614017B2

(12) United States Patent
Viavattine

(10) Patent No.: US 8,614,017 B2
(45) Date of Patent: Dec. 24, 2013

(54) ELECTROCHEMICAL CELL WITH ELECTRODE ELEMENTS THAT INCLUDE ALIGNMENT APERATURES

(75) Inventor: Joseph Viavattine, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 261 days.

(21) Appl. No.: 12/913,104

(22) Filed: Oct. 27, 2010

(65) Prior Publication Data

US 2012/0107670 A1    May 3, 2012

(51) Int. Cl.
*H01M 6/46* (2006.01)

(52) U.S. Cl.
USPC ............... 429/153; 429/1; 429/152; 429/178; 429/211; 429/246

(58) Field of Classification Search
USPC ......... 429/1, 59, 62, 115, 128, 129, 130, 152, 429/153, 158, 160, 161, 162, 178, 179–211, 429/233, 241, 246, 615; 29/623.4; 607/30, 607/36
See application file for complete search history.

(56) References Cited

U.S. PATENT DOCUMENTS

| | | | |
|---|---|---|---|
| 4,581,306 A * | 4/1986 | Hasenauer et al. | 429/123 |
| 5,230,967 A | 7/1993 | Radmall | |
| 5,419,982 A | 5/1995 | Tura | |
| 5,585,206 A | 12/1996 | Morris | |
| 5,862,035 A | 1/1999 | Farahmondi | |
| 6,004,692 A | 12/1999 | Muffoletto | |
| 7,179,562 B2 | 2/2007 | Zolotnik | |
| 2003/0040781 A1 * | 2/2003 | Larson et al. | 607/36 |
| 2003/0171784 A1 * | 9/2003 | Dodd et al. | 607/36 |
| 2004/0161669 A1 | 8/2004 | Zolotnik et al. | |
| 2006/0096082 A1 | 5/2006 | Aamodt | |
| 2006/0162149 A1 * | 7/2006 | Ha et al. | 29/623.1 |
| 2006/0166088 A1 | 7/2006 | Hokanson | |
| 2007/0150020 A1 | 6/2007 | Hokanson et al. | |
| 2007/0178383 A1 | 8/2007 | Viavattine | |
| 2009/0197180 A1 | 8/2009 | Viavattine | |

FOREIGN PATENT DOCUMENTS

| | | |
|---|---|---|
| DE | 102009005124 A1 | 7/2010 |
| WO | 2006068379 A1 | 6/2006 |

OTHER PUBLICATIONS

David Linden, Handbook of Batteries, 2002, McGraw-Hill, 3rd Edition, Chapter 15.11, p. 443-446.*
U.S. Appl. No. 12/913,079, by Joseph Viavattine, filed Oct. 27, 2010.
International Search Report and Written Opinion of international application No. PCT/US2011/033953, dated Jul. 25, 2011, 13 pp.

(Continued)

*Primary Examiner* — John S. Maples
*Assistant Examiner* — Jimmy K Vo

(57) ABSTRACT

A battery comprises a battery case forming a substantially sealed enclosure and an electrode stack within the enclosure. The electrode stack includes a first set of electrode elements and a second set of electrode elements. The electrode elements in the second set alternate with the electrode elements in the first set within the electrode stack. In addition, the electrode elements include coincident alignment apertures. The coincident alignment apertures are configured to restrict rotation of the electrode elements to align the electrode elements when the alignment apertures are positioned over mating alignment protrusions during assembly of the electrode stack. The battery further comprises a feedthrough including a feedthrough pin extending through the battery case. The feedthrough pin is electrically coupled to the electrode stack and serves as a positive terminal for the battery.

21 Claims, 8 Drawing Sheets

(56) References Cited

OTHER PUBLICATIONS

Non-Final Office Action from U.S. Appl. No. 12/913,079, dated Nov. 23, 2012, 19 pp.

Amendment from related U.S. Appl. No. 12/913,079, filed Feb. 21, 2013 (15 pages).

Office Action from U.S. Appl. No. 12/913,079 dated Apr. 25, 2013 (19 pages).

International Preliminary Report on Patentability from PCT/US2011/033953 dated May 10, 2013 (10 pages).

Office Action from U.S. Appl. No. 12/913,079, dated Oct. 24, 2013, 15 pp.

\* cited by examiner

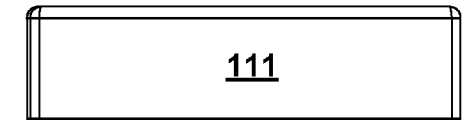
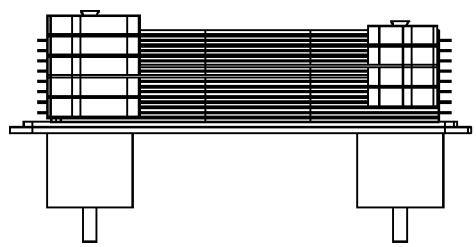
FIG. 7B
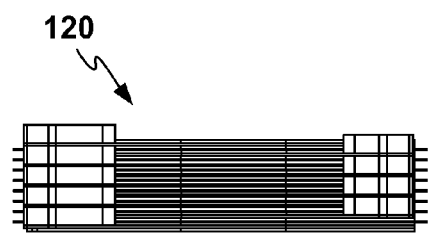
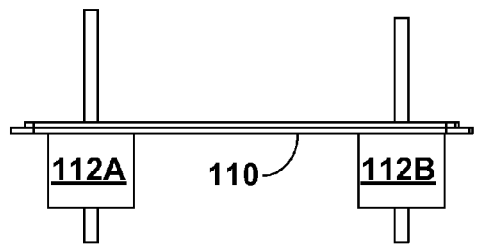
FIG. 7A
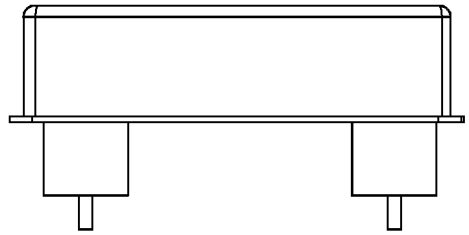
FIG. 7C

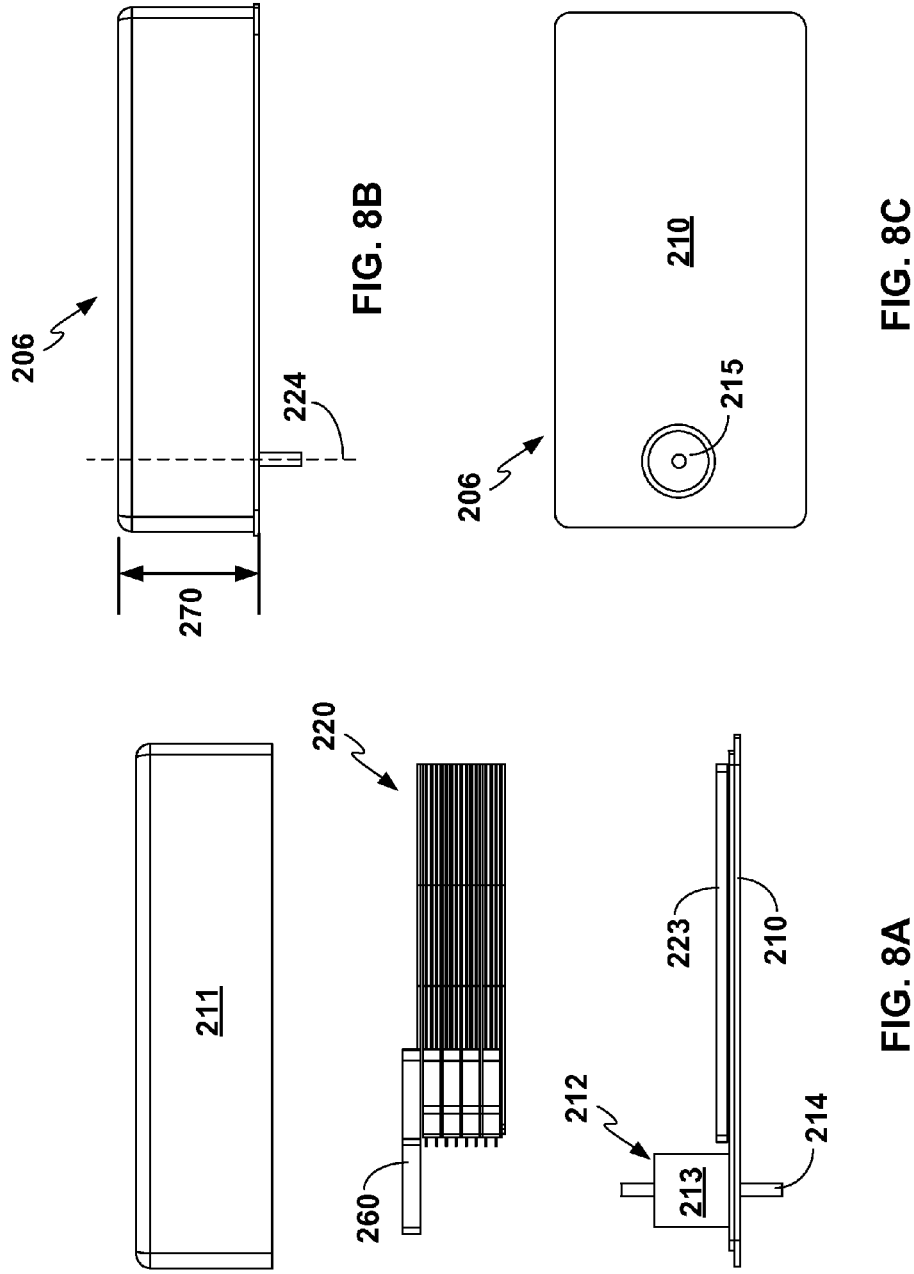

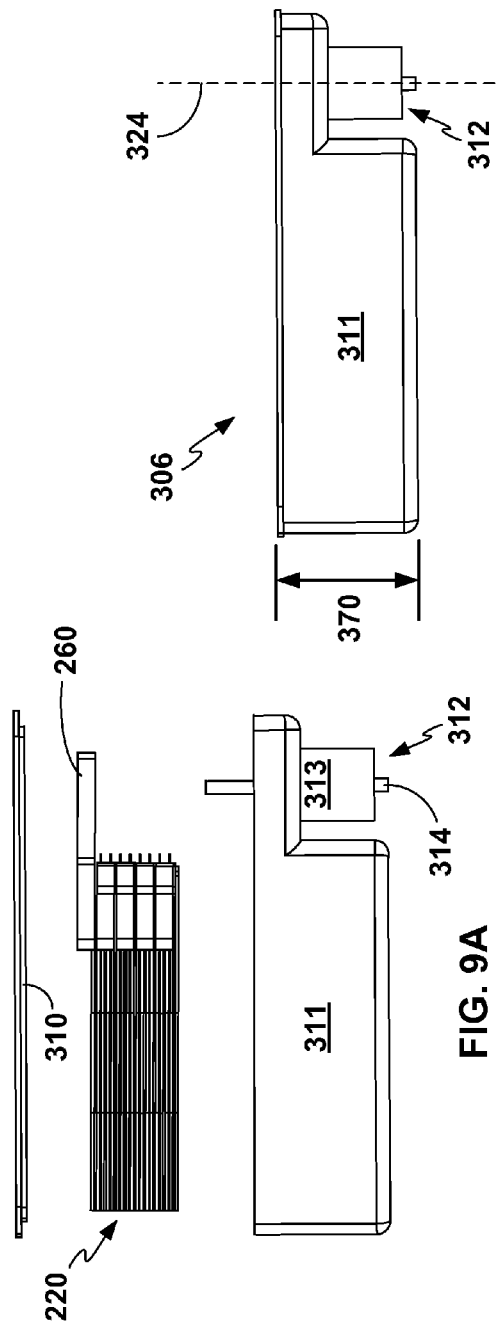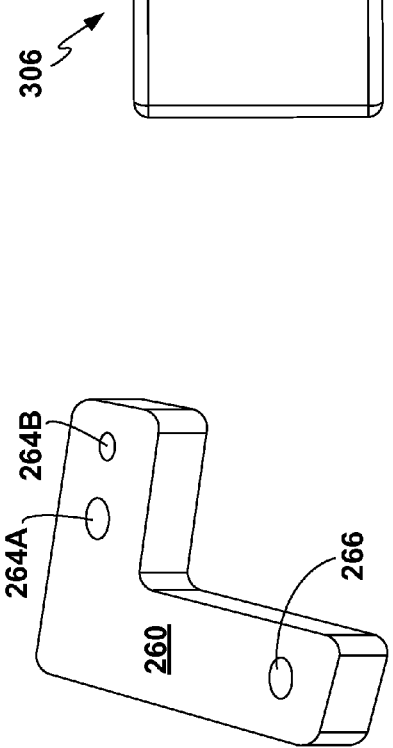

ELECTROCHEMICAL CELL WITH ELECTRODE ELEMENTS THAT INCLUDE ALIGNMENT APERATURES

TECHNICAL FIELD

This disclosure generally relates to electrochemical cells, and more particularly, but without limitation, to electrochemical cells for use in implantable medical devices.

BACKGROUND

Implantable medical devices (IMDs) may perform a variety of functions, including patient monitoring and therapy delivery. In general, it is desirable to design an IMD to be as small as possible, e.g., in terms of volume, footprint, and/or thickness, while still effectively performing its intended function. For example, decreasing the size of an IMD can increase the number of possible locations in which the IMD can be practically implanted. In addition, a smaller IMD can limit the extensiveness of surgery, reduce the likelihood of infection or rejection of the implant, and improve the comfort, and in some cases cosmetic appearance, of a patient after implantation. In other words, a smaller IMD may be more clinically acceptable than a larger IMD.

Examples of IMDs include implantable pulse generators (IPGs) and implantable cardioverter-defibrillators (ICDs). IPGs and ICDs comprise, among other things, a control module, a capacitor, and a battery that are housed in a hermetically sealed container. The battery includes a case, a liner, an electrode assembly, electrolyte, and at least one feedthrough extending through the case that serves as a battery terminal. The liner insulates the electrode assembly from the case. The electrode assembly includes electrodes, an anode and a cathode, with a separator therebetween.

SUMMARY

This disclosure includes electrochemical cells such as a battery in an implantable medical device (IMD). In one example, the battery includes an electrode assembly that comprises a set of plate electrodes. Each plate electrode includes a current collector with a tab extending there from and electrode material (also referred to as active material) disposed over the current collector. The battery may include spacers placed between adjacent tabs. The spacers ensures tabs are not bent when a set of tabs are connected during a subassembly process. The tabs and the spacers may form coincident apertures to receive a feedthrough pin of a feedthrough assembly of the battery. In some examples, the battery may include a feedthrough serving as a negative terminal in addition to a feedthrough serving as a positive terminal. In other examples, the battery may not include a distinct negative battery terminal and case of the battery may serve as the negative battery terminal.

This disclosure further includes techniques for aligning the plate electrodes and the spacers during assembly of an electrode stack for the battery. In particular, the tabs and the spacers may each include coincident alignment apertures to facilitate aligning the components of the electrode stack on an alignment fixture during assembly of the electrode stack.

In one example, this disclosure is directed to a battery comprising: a battery case forming a substantially sealed enclosure; an electrode stack within the enclosure, the electrode stack including a first set of electrode elements and a second set of electrode elements, the electrode elements in the second set alternating with the electrode elements in the first set within the electrode stack. The first set of electrode elements combine with the second set of electrode elements to form at least one voltaic cell. The battery further comprises a first set of conductive tabs including a conductive tab that extends from each of the electrode elements in the first set, wherein each of the conductive tabs in the first set forms at least one alignment aperture. The alignment apertures in the first set are coincident with each other. The coincident alignment apertures in the first set are configured to restrict rotation of the electrode elements in the first set to align the electrode elements in the first set with each other when the alignment apertures in the first set are positioned over a first set of one or more mating alignment protrusions. The battery further comprises a second set of conductive tabs including a conductive tab that extends from each of the electrode elements in the second set, wherein each of the conductive tabs in the second set forms at least one alignment aperture. The alignment apertures in the second set are coincident with each other. The coincident alignment apertures in the second set are configured to restrict rotation of the electrode elements in the second set to align the electrode elements in the second set with each other when the alignment apertures in the second set are positioned over a second set of one or more mating alignment protrusions. The battery further comprises a feedthrough including a feedthrough pin extending through the battery case. The feedthrough pin is electrically coupled to the first set of conductive tabs and serves as a terminal for the battery.

In another example, this disclosure is directed to a battery comprising: a battery case forming a substantially sealed enclosure; and an electrode stack within the enclosure, the electrode stack including a first set of plate electrodes and a second set of plate electrodes, the plate electrodes in the second set alternating with the plate electrodes in the first set within the electrode stack. The plate electrodes in the first and second sets of plate electrodes each includes a conductive substrate serving as a current collector, and an electrode material disposed over the current collector, wherein the conductive substrate includes a conductive tab that does have the electrode material coating. The electrode stack includes a first set of one or more spacers that are positioned between each adjacent tab of the conductive tabs in the first set of plate electrodes. The electrode stack further includes a second set of one or more spacers that are positioned between each adjacent tab of the in the second set of plate electrodes. The conductive tabs in the first set of plate electrodes and the first set of spacers are aligned to form a first coincident alignment aperture that extends through the first set of plate electrodes and the first set of spacers. The first coincident alignment aperture is configured to restrict rotation of the plate electrodes in the first set of plate electrodes to align the plate electrodes in the first set with each other when the conductive tabs in the first set of plate electrodes are positioned over a first set of one or more mating alignment protrusions during assembly of the electrode stack. The conductive tabs in the second set of plate electrodes and the second set of spacers are aligned to form a second coincident alignment aperture that extends through the second set of plate electrodes and the second set of spacers. The second coincident alignment aperture is configured to restrict rotation of the plate electrodes in the second set of plate electrodes to align the plate electrodes in the second set with each other when the conductive tabs in the second set of plate electrodes are positioned over a second set of one or more mating alignment protrusions during assembly of the electrode stack. The battery further comprises a feedthrough including a feedthrough pin extending through the battery case. The feedthrough pin is electrically coupled to the first set of conductive tabs and serves as a positive terminal for the battery; and an electrically conductive jumper in electrical contact with at least one of the first set of conductive tabs and with the feedthrough pin to electrically couple the feedthrough pin to the first set of electrode elements. The jumper includes at least one jumper alignment aperture, wherein the jumper alignment aperture is coincident with the alignment apertures in the first set, wherein the jumper alignment aperture is configured to restrict rotation of the jumper and locate the jumper relative to the electrode stack when the jumper alignment aperture is positioned over the first set of one or more mating alignment protrusions during assembly of the electrode stack. The feedthrough further includes a ferrule sealed to the case and an insulator separating the ferrule from the feedthrough pin, wherein a majority of the ferrule is located within the enclosure.

In another example, this disclosure is directed to a battery comprising: a battery case forming a substantially sealed enclosure; and an electrode stack within the enclosure, the electrode stack including a first set of plate electrodes and a second set of plate electrodes, the plate electrodes in the second set alternating with the plate electrodes in the first set within the electrode stack. The plate electrodes in the first and second sets of plate electrodes each includes a conductive substrate serving as a current collector, and an electrode material disposed over the current collector, wherein the conductive substrate includes a conductive tab that does have the electrode material coating. The electrode stack includes a first set of one or more spacers are positioned between each adjacent tab of the conductive tabs in the first set of plate electrodes. The electrode stack further includes a second set of one or more spacers are positioned between each adjacent tab of the in the second set of plate electrodes. The conductive tabs in the first set of plate electrodes and the first set of spacers are aligned to form a first coincident alignment aperture that extends through the first set of plate electrodes and the first set of spacers. The first coincident alignment aperture is configured to restrict rotation of the plate electrodes in the first set of plate electrodes to align the plate electrodes in the first set with each other when the conductive tabs in the first set of plate electrodes are positioned over a first set of one or more mating alignment protrusions during assembly of the electrode stack. The conductive tabs in the second set of plate electrodes and the second set of spacers are aligned to form a second coincident alignment aperture that extends through the second set of plate electrodes and the second set of spacers. The second coincident alignment aperture is configured to restrict rotation of the plate electrodes in the second set of plate electrodes to align the plate electrodes in the second set with each other when the conductive tabs in the second set of plate electrodes are positioned over a second set of one or more mating alignment protrusions during assembly of the electrode stack. The battery further comprises a feedthrough including a feedthrough pin extending through the battery case, wherein the feedthrough pin is electrically coupled to the first set of conductive tabs and serves as a positive terminal for the battery; and an electrically conductive jumper in physical contact with at least one of the first set of conductive tabs and with the feedthrough pin to electrically couple the feedthrough pin to the first set of electrode elements. The jumper includes at least one jumper alignment aperture, wherein the jumper alignment aperture is coincident with the alignment apertures in the first set, wherein the jumper alignment aperture is configured to restrict rotation of the jumper and locate the jumper relative to the electrode stack when the jumper alignment aperture is positioned over the first set of one or more mating alignment protrusions during assembly of the electrode. The feedthrough further includes a ferrule sealed to the case and an insulator separating the ferrule from the feedthrough pin, wherein a majority of the ferrule is located outside the enclosure. The battery case provides a thickness measured along the shortest dimension of the battery case. The feedthrough is parallel the shortest dimension of the battery case, and the feedthrough does not extend beyond the thickness of the battery case.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIGS. 7A-7C illustrate steps for assembling a battery including the battery cover and the electrode stack of FIG. 2.

FIGS. 8A-8C illustrate a battery including a feedthrough including a ferrule located substantially within the enclosure formed by the battery case.

FIGS. 9A-9C illustrate a battery including a feedthrough including a ferrule that does not extend beyond the thickness of the battery case.

FIG. 10 illustrates a jumper from the batteries shown in FIGS. 8A-9C.

DETAILED DESCRIPTION

Figure 1:
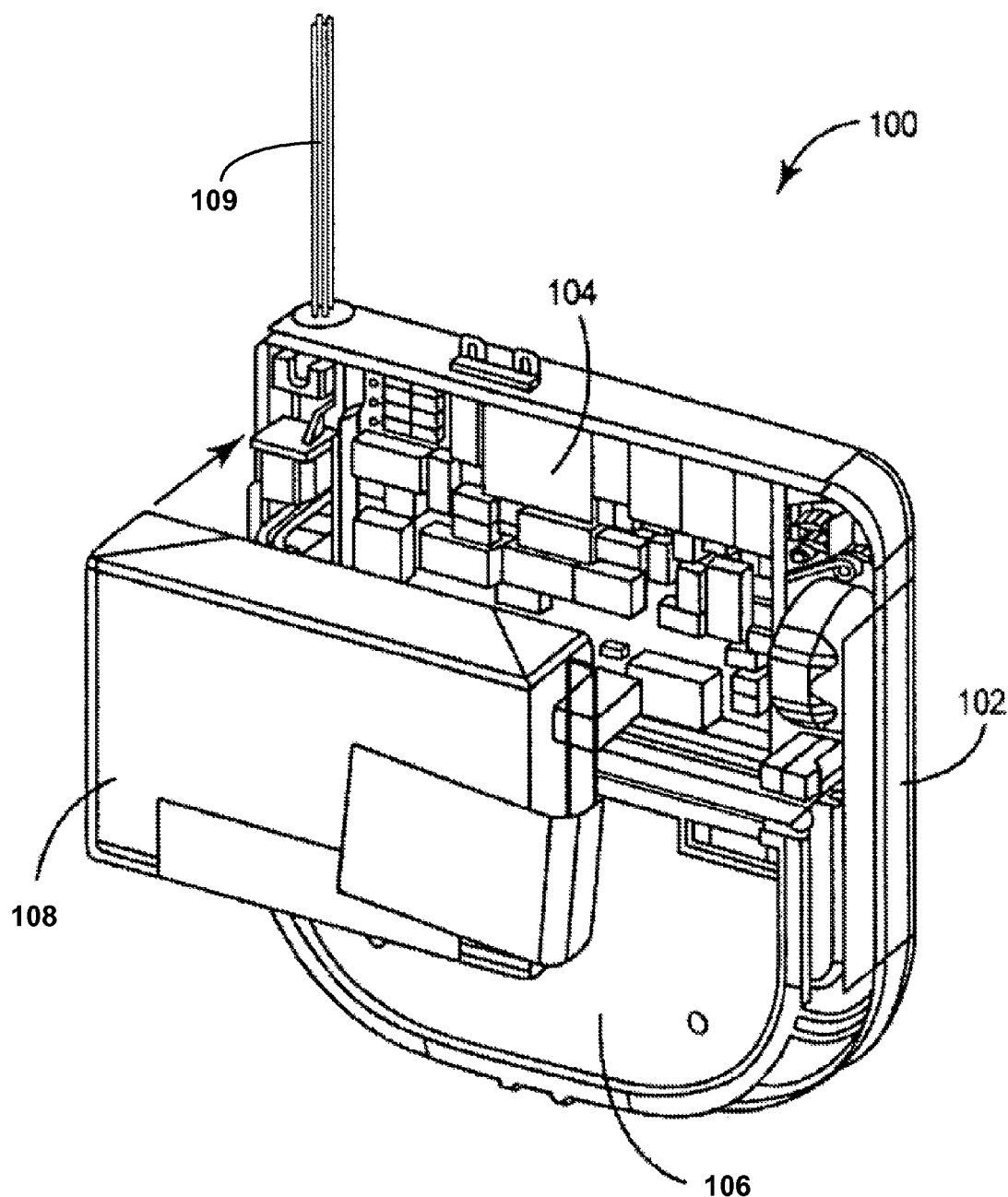
FIG. 1 is a cutaway perspective view of an implantable medical device (IMD) including a battery.

FIG. 1 depicts an IMD 100, which may be an implantable pulse generator (IPG, e.g., a pacemaker, or an implantable cardioverter-defibrillator (ICD, as examples. IMD 100 includes a case 102, a control module 104, a battery 106 and capacitor(s) 108. Control module 104 controls one or more sensing and/or stimulation functions of IMD 100, which functions may be performed via leads 109. Battery 106 charges capacitor(s) 108 and powers control module 104.

Figure 2:
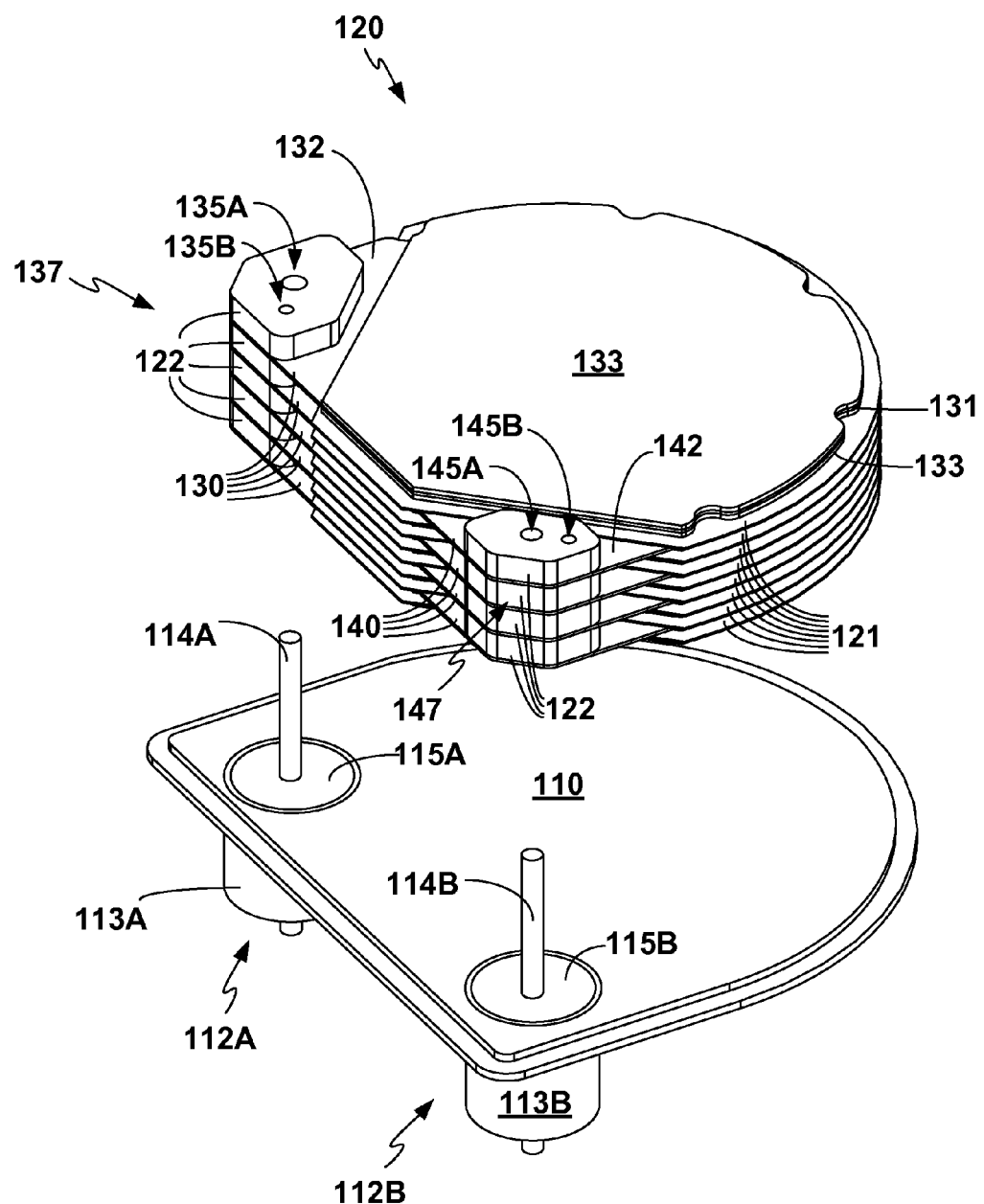
FIG. 2 illustrates an exploded perspective view of a battery cover and an electrode stack.
Figure 3:
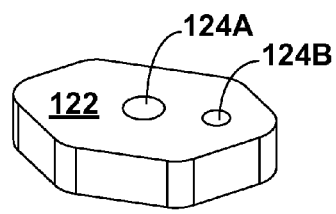
FIG. 3 illustrates a spacer of the electrode stack of FIG. 2.
Figure 4:
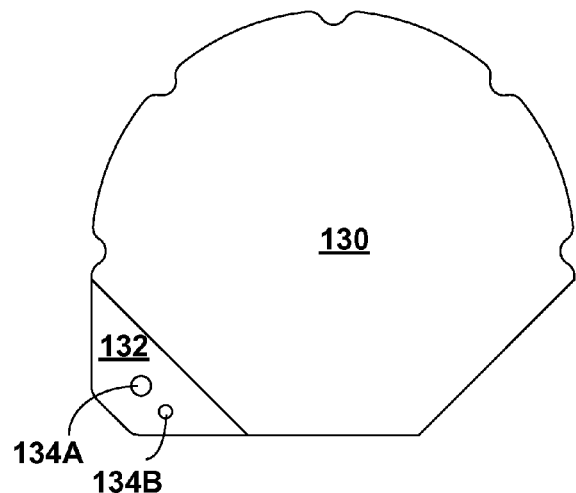
FIGS. 4 and 5 illustrate anode and cathode plate electrodes of the electrode stack of FIG. 2.
Figure 5:
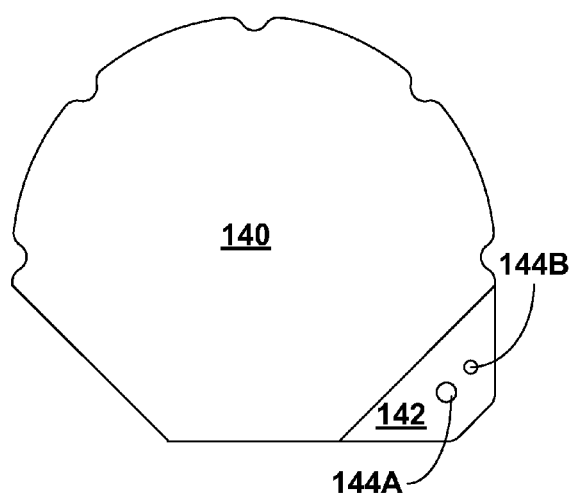

FIGS. 2-5 and 7A-7C illustrate components of battery 106. In particular, FIG. 2 illustrates an exploded perspective view of battery cover 110 and electrode stack 120. FIG. 3 illustrates one of the spacers 122 of electrode stack 120, while FIG. 4 illustrates an anode plate electrode 130 of electrode stack 120, and FIG. 5 illustrates a cathode plate electrode 140 of electrode stack 120. The anode plate electrodes 130 and cathode plate electrodes 140 are the electrode elements of battery 106. In some examples, anode plate electrodes 130 and cathode plate electrodes 140 may be substantially planar, in other examples, anode plate electrodes 130 and cathode plate electrodes 140 may be curved along one or more axis.

Battery 106 includes a battery case forming a substantially sealed enclosure with casement 111 (FIG. 7B) and top cover 110. As shown in FIG. 2, feedthroughs 112A and 112B ("feedthroughs 112") extend through top cover 110 and each include one of ferrules 113A, 113B ("ferrules 113"), one of feedthrough pins 114A, 114B ("feedthrough pins 114") and one of insulators 115A, 115B ("insulators 115"). In some examples, feedthrough pins 114 have diameters of less than 0.050 inches, such as a diameter of no greater than about 0.030 inches, such as a diameter of about 0.021 inches or a diameter of about 0.012 inches. Battery 106 further includes electrode stack 120, which is within the enclosure formed by the battery case. In some examples, battery 106 includes a fill port (not shown) as well as a liquid electrolyte within the enclosure. In some examples, battery 106 may be an organic electrolyte battery 106.

Electrode stack 120 includes a first set of plate electrodes 130 and a second set of plate electrodes 140. Positioned between each adjacent plate electrode 130 and plate electrode 140 is one of separators 121. Plate electrodes 130 form the cathode of battery 106, whereas plate electrodes 140 form the anode of battery 106 such that plate electrodes 130 combine with plate electrodes 140 to form a voltaic cell. Plate electrodes 130 alternate with plate electrodes 140 within electrode stack 120.

Each of plate electrodes 130 and plate electrodes 140 includes an electrically conductive substrate serving as a current collector. The electrically conductive substrate may be made of a metal, such alloys of copper, titanium, aluminum etc. As an example, the conductive substrate of the top plate electrode 130 is represented by reference numeral 131 in FIG. 2. An electrode material is disposed over the current collector in each of plate electrodes 130 and plate electrodes 140. As an example, the electrode material of the top plate electrode 130 is represented by reference numerals 133 in FIG. 2. In battery 106, the conductive substrates are substantially flat, and may include holes or other features to facilitate adhesion between the conductive substrate and the electrode material.

Each anode plate electrode 130 includes a current collector, such as current collector 131, a tab 132 extending there from, and electrode material disposed over the current collector. Tab 132 comprises conductive material (e.g. copper, titanium, aluminum etc.). In some examples, the current collector may be a unitary component with a tab 132. The electrode material, such as electrode material 133, includes elements from Group IA, IIA or IIIB of the periodic table of elements (e.g. lithium, sodium, potassium, etc.), alloys thereof, intermetallic compounds (e.g. Li—Si, Li—B, Li—Si—B etc.), or an alkali metal (e.g. lithium, etc.) in metallic form. In a further example, such as with a rechargeable cell, the electrode material of the anode plate electrode 130 may be lithium cobalt oxide or other suitable electrode material. The conductive substrate of anode plate electrode 130 may comprise nickel, titanium, copper an alloy thereof or other suitable conductive material. In some examples, a separator 121 may be coupled to the electrode material at the top and bottom of anode plate electrodes 130.

Each cathode plate electrode 140 is constructed in a similar manner as the anode plate electrodes 130. A cathode plate electrode 140 includes a conductive substrate serving as a current collector, a tab 142 (FIG. 5) extending there from and an electrode material disposed over the current collector. In some examples, the current collector may be a unitary component with a tab 142. The electrode material of the cathode plate electrodes 140 includes metal oxides (e.g. vanadium oxide, silver vanadium oxide (SVO), manganese dioxide etc.), carbon monofluoride and hybrids thereof (e.g., $CF_x$+ $MnO_2$), combination silver vanadium oxide (CSVO), lithium ion, other rechargeable chemistries, or other suitable compounds. In a further example, such as with a rechargeable cell, the electrode material of the cathode plate electrode 140 may be lithium titanate, graphite or other suitable electrode material. The conductive substrate of cathode plate electrode 140 may be, for example, titanium, aluminum, nickel or other suitable materials.

While the example chemistries provi. Our current chemistries are lithium cobalt oxide for the positive and either lithium titanate or graphite for the negative.

As previously mentioned, each anode plate electrode 130 includes a tab 132. A spacer 122 is positioned between each adjacent tab 132. Similarly, each cathode plate electrode 140 includes a tab 142, and a spacer 122 is positioned between each adjacent tab 142. Spacers 122 function to mitigate bending of tabs 132 and 142 during assembly of electrode stack 120. Spacers 122 may also be formed from a conductive material such as titanium, aluminum/titanium clad metal or other suitable materials. Accordingly, spacers 122 may also serve to electrically connect anode plate electrodes 130 via tabs 132 with each other as well as electrically connect cathode plate electrodes 140 via tabs 142 with each other within electrode stack 120.

As previously mentioned, tabs 132, 142 may be a unitary component with the electrically conductive substrates of anode plate electrode 130 and cathode plate electrode 140 respectively. In one example, tabs 132 may be formed by masking a portion of an electrically conductive substrate when depositing an electrode material, e.g., lithium, on the electrically conductive substrate of a plate electrode. The electrically conductive substrate may be masked by placing a material, such as a polymer between electrically conductive substrates and the electrode material. In some examples, the mask material may be die cut to provide precise masking of tabs 132 and 142.

The thickness of spacers 122 is dependent on the thicknesses of anode plate electrode 130 and cathode plate electrode 140. As an example, spacers 122 may have a thickness of less than 0.060 inches, such as a thickness of about 0.020 inches. In other examples, spacers 122 may have a thickness of between 0.10 inches to 0.060 inches. In a further example, such as in a rechargeable cell, spacers 122 may have a thickness of between 0.005 inches to 0.020 inches. For example, the electrode material of rechargeable cells may be formed using a slurry process, which can provide thinner electrode plates than with a pressed powder process more commonly used for making electrode plate in nonrechargeable cells. In general, the thickness of spacers should be selected to match the spacing between adjacent tabs 132 and adjacent tabs 142 when anode plate electrodes 130 and cathode plate electrodes 140 are stacked, e.g., directly on each other.

Further details and techniques suitable for the construction of electrode stack 120 are disclosed in United States Patent Publication Number 2009/0197180 by Viavattine et al., titled "SPACERS BETWEEN TABS OF PLATE ELECTRODES IN AN ELECTROCHEMICAL CELL FOR AN IMPLANTABLE MEDICAL DEVICE," the entire content of which is incorporated by reference herein.

As illustrated in FIG. 3, spacers 122 include alignment apertures 124A and 124B. In the set of spacers 122 between adjacent tabs 132, alignment apertures 124A are coincident with each other and with alignment apertures 134A (FIG. 4) of tabs 132 to form coincident aperture 135A (FIG. 2). Likewise, alignment apertures 124B are coincident with each other and with alignment apertures 134B of tabs 132 to form coincident aperture 135B. As shown in FIG. 7B, feedthrough pin 114A extends through the battery case and through incident aperture 135A and serves as a positive terminal for battery 106.

Similarly, in the set of spacers 122 between adjacent tabs 142, alignment apertures 124A are coincident with each other and with alignment apertures 144A of tabs 142 to form coincident aperture 145A. Likewise, alignment apertures 124B are coincident with each other and with alignment apertures 144B of tabs 142 to form coincident aperture 145B. Feedthrough pin 114B extends through the battery case and through incident aperture 145A and serves as a negative terminal for battery 106. In other examples, a battery may not include a distinct negative battery terminal and case of the battery may serve as the negative battery terminal.

Connecting feedthrough pins 114 directly to tabs 132 and 134 of plate electrodes 130 and 140 respectively provides for robust electrical connections between feedthrough pins 114 and plate electrodes 130 and 140. In addition connecting feedthrough pins 114 directly to tabs 132 and 134 of plate electrodes 130 and 140 respectively also serves to minimize the space in battery 106 required for feedthroughs 112 as well as limit heat generation caused by electrical resistance in the electrical connection between feedthrough pins 114 and plate electrodes 130 and 140. The design of tabs 132 and 142 also serves to limit electrical resistance in the electrical connection between feedthrough pins 114 and plate electrodes 130 and 140 because tabs 132 and 142 provide a wide electrical path between feedthrough pins 114 and plate electrodes 130 and 140 respectively.

Figure 6:
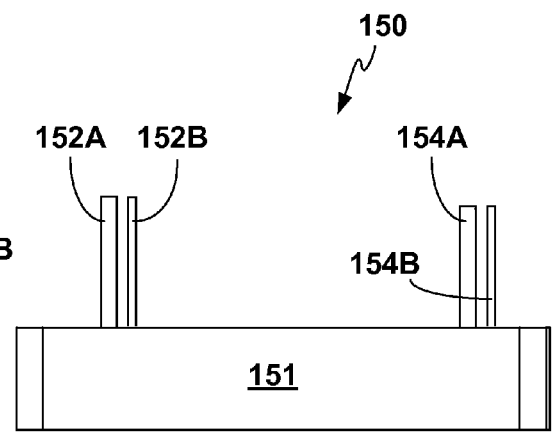
FIG. 6 illustrates an alignment fixture suitable for assembling the electrode stack of FIG. 2.

FIG. 6 illustrates an example alignment fixture 150, which is suitable for stacking and aligning components of electrode stack 120 during assembly. Each anode plate electrode 130, cathode plate electrode 140 and spacer 122 in electrode stack 120 includes alignment apertures to facilitate stacking the components of electrode stack 120 in alignment on alignment fixture 150. Alignment fixture 150 includes platform 151 and alignment pins 152A, 152B, 154A and 154B, each extending in a common direction from platform 151. Alignment pins 152A, 152B ("alignment pins 152") serve as mating protrusions for coincident apertures 135A and 135B, including alignment apertures 134 in anode plate electrodes 130 as well as alignment apertures 124 in the spacers 122 positioned between adjacent tabs 132. Likewise, alignment pins 154A, 154B ("alignment pins 154") serve as mating protrusions for coincident apertures 145A and 145B, including alignment apertures 144 in cathode plate electrodes 140 as well as alignment apertures 124 in the spacers 122 positioned between adjacent tabs 142.

During the assembly process of electrode stack 120, the components of electrode stack 120, including each anode plate electrodes 130, cathode plate electrode 140 and spacer 122 are positioned over alignment pins 152 and 154 and stacked on alignment fixture 150. Anode plate electrodes 130 alternate with cathode plate electrode 140 when stacked on alignment fixture 150. Plate electrodes are stacked on alignment fixture 150 such that alignment apertures 134 of anode plate electrodes 130 are positioned over alignment pins 152, and alignment apertures 144 of cathode plate electrodes 140 are positioned over alignment pins 154. Spacers 122 positioned between adjacent tabs 132 on alignment pins 152 and between adjacent tabs 142 on alignment pins 154.

Alignment pins 152 facilitate proper alignment of anode plate electrodes 130 by interacting with alignment apertures 134 in anode plate electrodes 130 to restrict rotation of anode plate electrodes 130 to align anode plate electrodes 130 as well as the spacers 122 positioned between adjacent tabs 132 with each other. Similarly, alignment pins 154 facilitate proper alignment of cathode plate electrodes 140 by interacting with alignment apertures 144 in cathode plate electrodes 140 to restrict rotation of cathode plate electrodes 140 to align cathode plate electrodes 140 as well as the spacers 122 positioned between adjacent tabs 142 with each other.

Alignment apertures 134 in anode plate electrodes 130 are orientated differently alignment apertures 144 in cathode plate electrodes 140. In particular, alignment apertures 134 in anode plate electrodes 130 are orientated differently than alignment apertures 144 in cathode plate electrodes 140 to prevent interchanging an anode plate electrodes 130 with a cathode plate electrodes 140 within the electrode stack 120 during assembly of the electrode stack 120 on alignment fixture 150 and vice versa. Simply, an anode plate electrode 130 will not fit in the place of cathode plate electrode 140 on alignment fixture 150. However, the configurations of alignment apertures 134 and alignment apertures 144 is similar in that the same spacer 122 may be used in between adjacent tabs 132 and in between adjacent tabs 142 on alignment fixture 150. In particular, a spacer 122 positioned over alignment pins 152 (suitable for placement in-between adjacent tabs 132) merely needs to be rotated to positioned over alignment pins 154 (suitable for placement in-between adjacent tabs 142).

Once the components of electrode stack 120 including each anode plate electrode 130, cathode plate electrode 140 and spacer 122 are positioned appropriately on alignment fixture 150 to form electrode stack 120, tabs 132 and spacers 122 adjacent tabs 132 may be welded to each other with a single weld, such as a laser weld to form a weld joint in weld zone 137 (FIG. 2), a beveled corner of electrode stack 120. Likewise, tabs 142 and spacers 122 adjacent tabs 142 may also be welded to each other with one additional to form a weld joint in weld zone 147. In some examples, laser welding may occur while the components of electrode stack 120 remain on alignment fixture 150. In other examples, the relative alignment of the components of electrode stack 120 provided by alignment fixture 150 may be maintained during welding even though the components of electrode stack 120 may be removed from alignment fixture 150 prior to welding operations.

FIGS. 7A-7C illustrate steps for assembling battery 106. The steps for assembling battery 106 may be automated, e.g., using pick-and-place machinery, performed manually, or performed with a combination of automated and manual steps. As discussed above, the components of electrode stack 120 are stacked and aligned, e.g., using an alignment fixture such as alignment fixture 150. The components of electrode stack 120 may also be connected using welds, e.g., by laser welding in weld zones 137 and 147, either on an alignment fixture or after removing the components of electrode stack 120 from the alignment fixture, but while maintaining the relative alignment provided by the alignment fixture. In some examples, an insulator may be placed over electrode stack 120 while the components of electrode stack 120 remain on the alignment fixture. The insulator serves to electrically isolate the electrode stack from the battery case once battery 106 is assembled. An exemplary insulator is shown as insulator 223 in FIG. 8A.

As shown in FIG. 7A, cover 110 includes feedthroughs 112 extending there through. Electrode stack 120 is positioned over cover 110 and slid over feedthrough pins 114 such that pin 114A extends through coincident aperture 135A in tabs 132, and pin 114B extends through coincident aperture 145A in tabs 142. The end of feedthrough pin 114A may be welded to electrode stack 120 opposite coincident aperture 135A, and the end of feedthrough pin 114B may be welded to electrode stack 120 opposite coincident aperture 145A. For example, spot welding may be used to electrically and mechanically couple feedthrough pins 114 to electrode stack 120. Alternatively or in addition to spot welding, the ends of feedthrough pins 114 may be crimped to secure feedthrough pins 114 to electrode stack 120. In some examples, welding in weld zones 137 and 147 may occur only after placing the components electrode stack 120 over feedthrough pins 114 such that welding in weld zones 137 and 147 may occur at the same time as the welding of feedthrough pins 114 to electrode stack 120.

As shown in FIG. 7B, once electrode stack 120 is secured to cover 110, casement 111 is positioned over electrode stack 120. As shown in FIG. 7C, the interface between cover 110 and casement 111 may then be welded to provide battery 106 with a substantially sealed enclosure including electrode stack 120. In some examples, battery 106 may also include a fill port (not shown) and liquid electrolyte may then be added to battery 106 via the fill port.

FIGS. 8A-8C illustrate components of battery 206. Battery 206 is similar to battery 106. For brevity, features of battery 206 that are substantially similar to features previously discussed with respect to battery 106 are discussed in limited or no detail with respect to battery 206. Battery 206 includes electrode stack 220 and a case including cover 210 and casement 211. Cover 210 and casement 211 combine to form a substantially sealed enclosure containing electrode stack 220.

Battery 206 further includes feedthrough 212, which serves as a positive terminal of battery 206. Feedthrough 212 extends through cover 210, which is substantially flat. Feedthrough 212 includes ferrule 213, feedthrough pin 214 and insulator 215, which electrically isolates feedthrough pin 214 from ferrule 213. A majority of ferrule 213 is located within the enclosure of battery 206, for example, ferrule 213 may be located substantially within the enclosure of battery 206. The configuration of battery 206 allows feedthrough 212 to extend in a direction parallel to the thickness dimension of battery 206 without extending significantly beyond the thickness of battery 206. This allows battery 206 to provide a thinner overall provide than battery 106. However, the configuration of battery 206 may provide a lower overall energy density than that of battery 106 because of the space required within the enclosure of battery 206 for jumper 260.

Electrode stack 220 is substantially similar to electrode stack 120 except that electrode stack 220 connects to the positive terminal of battery 206 via jumper 260. For example, electrode stack 220 includes anode plate electrodes that alternate with cathode plate electrodes within electrode stack 220 with separators between adjacent anode plate electrodes and cathode plate electrodes. Electrode stack 220 also includes spacers between tabs of the plate electrodes and coincident alignment apertures to facilitate alignment of anode plate electrodes, cathode plate electrodes and spacers on an alignment fixture such as alignment fixture 150.

Jumper 260 is in electrical contact with the anode of electrode stack 220 as well as feedthrough pin 214, which serves as the positive terminal of battery 206. Battery 206 does not include a distinct negative terminal; instead, electrode stack 120 is electrically coupled to cover 210 (not shown), such that the case of battery 206 serves as the negative terminal of battery 206 (also referred to as case negative).

Details of jumper 260 are illustrated in FIG. 10. Jumper 260 includes alignment apertures 264A and 264B ("alignment apertures 264"). Within electrode stack 220, alignment apertures 264 align with coincident alignment apertures within tabs of anode plate electrodes of electrode stack 220. Alignment apertures 264 are configured to restrict rotation of jumper 260 and locate jumper 260 relative to the electrode stack 220 when alignment apertures 264 are positioned over mating alignment protrusions, e.g., such as alignment protrusions 152, during assembly of electrode stack 220. For example, jumper 260 may be located on an alignment fixture, such as alignment fixture 150, with the components of electrode stack 220.

Jumper 260 may be formed from a conductive material such as titanium, aluminum/titanium clad metal or other suitable materials. Jumper 260 may secured to tabs of anode plate electrodes of electrode stack 220 during the assembly process of electrode stack 220. For example, jumper 260 may secured to tabs of anode plate electrodes of electrode stack 220 during a welding operation to secure the tabs of anode plate electrodes of electrode stack 220 to each other.

The configuration of jumper 260 facilitates customizable placement of feedthrough 212 on the battery case without altering the components of electrode stack 220. For example, the same electrode stack 220 may be used with multiple jumper configurations to locate a feedthrough at different positions on a battery case. Such configurability may be useful to reduce the size and/or cost of implantable medical devices including a battery such as battery 206 by optimizing the placement of the feedthrough according to the configuration other components within an implantable medical device. While battery 206 only includes a single feedthrough and a single jumper, the same techniques discussed with respect to jumper 260 and feedthrough 212 may be used to provide a second feedthrough serving as a negative terminal for battery 206.

FIGS. 8A-8C illustrate steps for assembling battery 206. The steps for assembling battery 206 may be automated, e.g., using pick-and-place machinery, performed manually, or performed with a combination of automated and manual steps. First, the components of electrode stack 220 are stacked and aligned in combination with jumper 260, e.g., using an alignment fixture such as alignment fixture 150. The components of electrode stack 120 as well as jumper 260 may also be connected using welds, e.g., by laser welding either on an alignment fixture.

Cover 210 includes feedthrough 212 extending there through. Insulator 223 is located on the inside of cover 210 to electrically isolate electrode stack 220 from the battery case once battery 306 is assembled. Electrode stack 220 is positioned cover 110 and jumper 260 slid over feedthrough pin 214 such that pin 214 extends through feedthrough pin hole 266 (FIG. 10) in jumper 260.

The end of feedthrough pin 214 may be spot welded to jumper 260 opposite feedthrough pin hole 266 (FIG. 10) to and mechanically couple feedthrough pin 214 to jumper 260. Alternatively or in addition to spot welding, the end of feedthrough pin 214 may be crimped to secure feedthrough pin 214 to jumper 260.

As shown in FIG. 8A, once jumper 260 is secured to cover 210, casement 211 is positioned over electrode stack 220 and jumper 260. As shown in FIGS. 8B and 8C, the interface between cover 210 and casement 211 may then be welded to provide battery 206 with a substantially sealed enclosure containing electrode stack 220, jumper 260 and a majority of feedthrough 213. In some examples, battery 206 may also include a fill port (not shown) and liquid electrolyte may then be added to battery 206 via the fill port.

The case of battery 206 provides thickness 270, which is measured along the shortest dimension of the battery case. A longitudinal axis 224 of feedthrough 212 is parallel to thickness 270 and ferrule 213 of feedthrough 212 does not extend beyond the thickness 270. This allows battery 206 to provide a thinner overall profile than battery 106.

FIGS. 9A-9C illustrate components of battery 306. Battery 306 is similar to batteries 106 and 206. For brevity, features of battery 306 that are substantially similar to features previously discussed with respect to batteries 106 and 206 are discussed in limited or no detail with respect to battery 306. Battery 306 includes electrode stack 220 and a case including cover 310 and casement 311. Electrode stack 220 in battery 306 may be substantially the same as electrode stack 220 in battery 206. Cover 310 and casement 311 combine to form a substantially sealed enclosure containing electrode stack 220.

Battery 306 further includes feedthrough 312, which serves as a positive terminal of battery 306. Feedthrough 312 extends through casement 311. Feedthrough 312 includes ferrule 313, feedthrough pin 314 and insulator 315, which electrically isolates feedthrough pin 314 from ferrule 313.

The case of battery 306 provides thickness 370, which is measured along the shortest dimension of the battery case. A longitudinal axis 324 of feedthrough 312 is parallel to thickness 370 and feedthrough 312 does not extend beyond the thickness 370. This allows battery 306 to provide a thinner overall profile than battery 106. As compared to battery 206, battery 306 provides feedthrough 312 with an exposed ferrule 313, which may facilitate a more robust or simpler electrical connection between battery 306 and other electrical components within an implantable medical device.

The assembly process of battery 306 may be more difficult than the assembly process of battery 206 in that electrode stack 220 is not exposed in casement 311 once jumper 260 is secured to feedthrough pin 314. As one example, the configuration of battery 306 does not facilitate welding tabs of plate electrodes in electrode stack 220 to each other after positioning the components of electrode stack 220 in casement 311. In contrast, the configuration of battery 206 does allow welding tabs of plate electrodes in electrode stack 220 to each other after positioning the components of electrode stack 220 on cover 210. For this reason, welding jumper 260 to feedthrough pin 214 could occur at the same time as welding tabs of plate electrodes in electrode stack 220 to each other during the assembly of battery 206. In contrast, welding tabs of plate electrodes in electrode stack 220 to each other during the assembly of battery 306 should occur prior to placing electrode stack 220 in casement 111 and prior to welding jumper 260 to feedthrough pin 314.

As shown in FIG. 9B, once jumper 260 is secured to casement 311, cover 310 is positioned over electrode stack 220 and jumper 260. As shown in FIGS. 9B and 9C, the interface between cover 310 and casement 311 may then be welded to provide battery 306 with a substantially sealed enclosure containing electrode stack 220 and jumper 260. In some examples, battery 306 may also include a fill port (not shown) and liquid electrolyte may then be added to battery 306 via the fill port.

Figure 11:
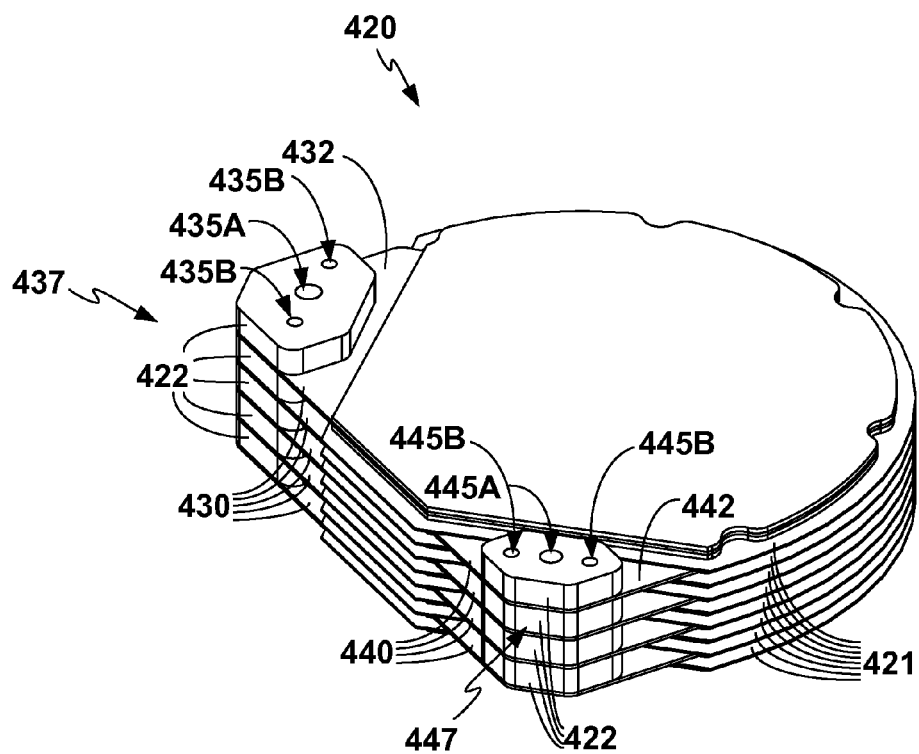
FIG. 11 illustrates an electrode stack.

FIG. 11 illustrate electrode stack 420. Electrode stack 420 is substantially similar to electrode stack 120 (FIG. 2) except that electrode stack 420 forms additional coincident apertures 435B and 445B. For brevity, details of electrode stack 420 that are the same as electrode stack 120 are discussed in limited detail with respect to electrode stack 420.

Electrode stack 420 includes a first set of plate electrodes 430 and a second set of plate electrodes 440. Positioned between each adjacent plate electrode 430 and plate electrode 440 is one of separators 421. Plate electrodes 430 form a cathode, whereas plate electrodes 440 form an anode. Each anode plate electrode 430 includes a current collector, a tab 432 extending there from, and electrode material disposed over the current collector. Each anode plate electrode 440 includes a current collector, a tab 442 extending there from, and electrode material disposed over the current collector. Plate electrodes 430 alternate with plate electrodes 440 within electrode stack 420.

Like spacers 122 in electrode stack 120, a spacer 422 is positioned between each adjacent tab 132 and 142. Spacers 422 function to mitigate bending of tabs 432 and 442 during assembly of electrode stack 420 as well as provide electrical connections between adjacent tabs.

The set of spacers 422 between adjacent tabs 432 provide alignment apertures that are coincident with alignment apertures of tabs 132 to form coincident apertures 435A and 435B. Likewise, the set of spacers 422 between adjacent tabs 442 provide alignment apertures that are coincident with alignment apertures of tabs 142 to form coincident apertures 445A and 445B. Coincident apertures 435A and 445A are each configured to receive a feedthrough pin, such as feedthrough pins 113A and 113B, whereas coincident apertures 435B and 445B are configured to receive alignment pins on an alignment fixture during the assembly of electrode stack 420.

Figure 12:
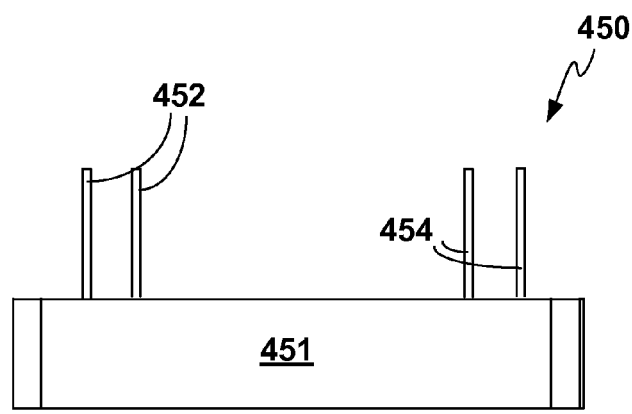
FIG. 12 illustrates an alignment fixture suitable for assembling the electrode stack of FIG. 11.

FIG. 12 illustrates alignment fixture 450, which is suitable for stacking and aligning components of electrode stack 420. Each anode plate electrode 430, cathode plate electrode 440 and spacer 422 in electrode stack 420 includes alignment apertures to facilitate stacking the components of electrode stack 420 in alignment on alignment fixture 450. Alignment fixture 450 includes platform 451 and alignment pins 452 and 454, each extending in a common direction from platform 451. Alignment pins 452 serve as mating protrusions for coincident apertures 435B. Likewise, alignment pins 454 serve as mating protrusions for coincident apertures 445B.

During the assembly process of electrode stack 420, the components of electrode stack 420, including each anode plate electrodes 430, cathode plate electrode 440 and spacers 422 are positioned over alignment pins 152 and 154 and stacked on alignment fixture 150. Anode plate electrodes 430 alternate with cathode plate electrode 440 when stacked on alignment fixture 450. Plate electrodes are stacked on alignment fixture 450 such that alignment apertures of anode plate electrodes 430 are positioned over alignment pins 452, and alignment apertures of cathode plate electrodes 440 are positioned over alignment pins 454. Spacers 422 positioned between adjacent tabs 432 on alignment pins 452 and between adjacent tabs 442 on alignment pins 454.

Alignment pins 452 facilitate proper alignment of anode plate electrodes 430 by interacting with alignment apertures in anode plate electrodes 430 to restrict rotation of anode plate electrodes 430 to align anode plate electrodes 430 as well as the spacers 422 positioned between adjacent tabs 432 with each other. Similarly, alignment pins 454 facilitate proper alignment of cathode plate electrodes 440 by interacting with alignment apertures 444 in cathode plate electrodes 440 to restrict rotation of cathode plate electrodes 440 to align cathode plate electrodes 440 as well as the spacers 422 positioned between adjacent tabs 442 with each other.

The alignment apertures in anode plate electrodes 430 may be orientated differently than alignment apertures in cathode plate electrodes 440 to prevent interchanging an anode plate electrode 430 with a cathode plate electrode 440 within the electrode stack 420 during assembly of the electrode stack 420 on alignment fixture 450 and vice versa.

Figure 13C:
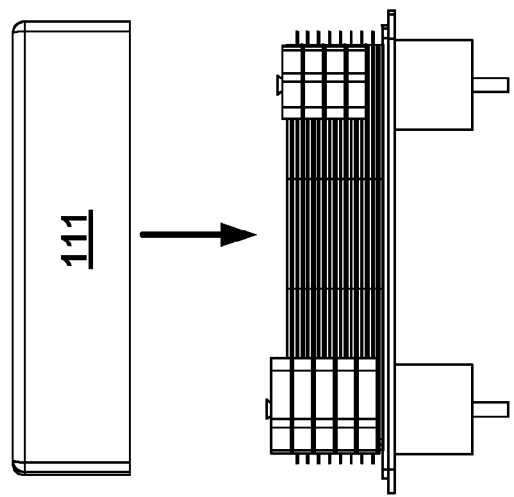
FIGS. 13A-13C illustrate steps for assembling a battery including the electrode stack of FIG. 11 using the alignment fixture of FIG. 12.
Figure 13B:
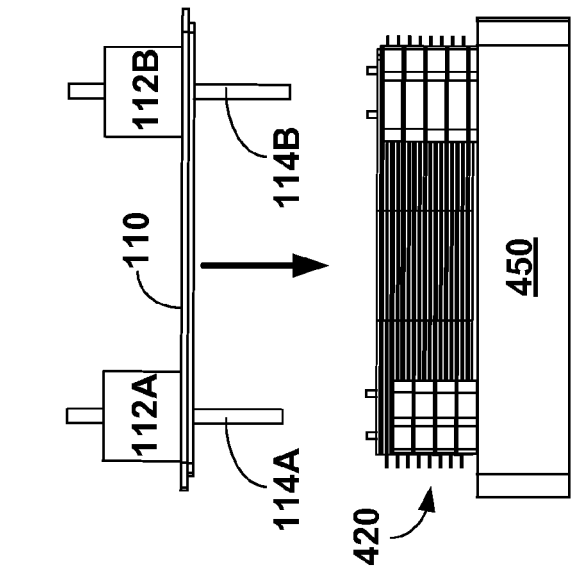
Figure 13A:
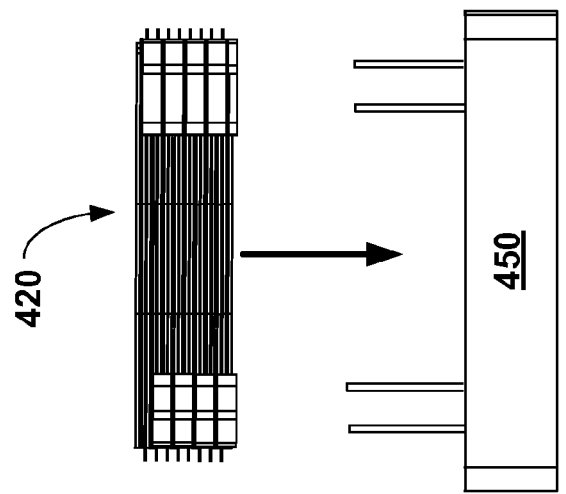

FIGS. 13A-13C illustrate steps for assembling a battery including electrode stack 420 using alignment fixture 450. The steps for assembling electrode stack 420 may be automated, e.g., using pick-and-place machinery, performed manually, or performed with a combination of automated and manual steps. As discussed above, the components of electrode stack 420 are stacked and aligned, e.g., using an alignment fixture such as alignment fixture 450. The components of electrode stack 420 may also be connected using welds, e.g., by laser welding in weld zones 437 and 447 (FIG. 11), on alignment fixture 450.

However, even after welding of anode plate electrodes 430 in weld zone 437 and cathode plate electrodes 440 in weld zone 447, the alignment of anode plate electrodes 430 relative to cathode plate electrodes 440 is not inherently secured without alignment fixture 450. Electrode stack 420 provides an advantage relative to electrode stack 120 in that electrode stack 420 may receive feedthrough pins 114 of feedthroughs 112 (FIG. 13B) while electrode stack 420 is still positioned on alignment stand 450. Once feedthrough pins 114 are mated to coincident apertures 435A and 445A of anode plate electrodes 430 and cathode plate electrodes 440 respectively, feedthroughs 112 and cover 110 serve to maintain the alignment of anode plate electrodes 430 relative to cathode plate electrodes 440.

As shown in FIG. 13A, electrode stack 420 is first assembled using alignment fixture 450. For example, assembly of electrode stack 420 may include welding of anode plate electrodes 430 in weld zone 437 and cathode plate electrodes 440 in weld zone 447. Next, as shown in FIG. 13B cover 110 is positioned over electrode stack 420 while the components of electrode stack 420 remain in alignment on alignment fixture 450. Positioning cover 110 over electrode stack 420 includes inserting feedthrough pins 114 such that pin 114A extends through coincident aperture 435A in tabs 432, and pin 414B extends through coincident aperture 445A in tabs 442.

The assembled cover 110 and electrode stack 420 are removed from alignment fixture 450. In addition, the end of feedthrough pin 114A may be welded and/or crimped to electrode stack 420 opposite coincident aperture 435A, and the end of feedthrough pin 414B may be welded and/or crimped to electrode stack 420 opposite coincident aperture 145A.

As shown in FIG. 13C, once electrode stack 420 is secured to cover 110, casement 111 is positioned over electrode stack 420. The interface between cover 110 and casement 111 may then be welded to provide a battery with a substantially sealed enclosure including electrode stack 420. In some examples, the battery may also include a fill port (not shown) and liquid electrolyte may then be added to the battery via the fill port.

Various examples of the invention have been described. These and other examples are within the scope of the following claims.

The invention claimed is:
1. A battery comprising:
a battery case forming a substantially sealed enclosure;
an electrode stack within the enclosure, the electrode stack including a first set of electrode elements and a second set of electrode elements, the electrode elements in the second set alternating with the electrode elements in the first set within the electrode stack,
wherein the first set of electrode elements combine with the second set of electrode elements to form at least one voltaic cell;
a first set of conductive tabs including a conductive tab that extends from each of the electrode elements in the first set, wherein each of the conductive tabs in the first set has at least two alignment apertures, wherein the alignment apertures in the first set are coincident with each other, wherein the coincident alignment apertures in the first set are configured to restrict rotation of the electrode elements in the first set to align the electrode elements in the first set with each other when the alignment apertures in the first set are positioned over a first set of one or more mating alignment protrusions;
a first set of one or more spacers, wherein the spacers in the first set are positioned between each adjacent tab of the first set of conductive tabs, wherein the spacers in the first set of spacers each form at least one coinciding spacer aperture, wherein the coinciding spacer aperture is in alignment with the coincident alignment apertures in the first set of conductive tabs;
a second set of conductive tabs including a conductive tab that extends from each of the electrode elements in the second set, wherein each of the conductive tabs in the second set has at least two alignment apertures, wherein the alignment apertures in the second set are coincident with each other, wherein the coincident alignment apertures in the second set are configured to restrict rotation of the electrode elements in the second set to align the electrode elements in the second set with each other when the alignment apertures in the second set are positioned over a second set of one or more mating alignment protrusions;
a second set of one or more spacers, wherein the spacers in the second set are positioned between each adjacent tab of the second set of conductive tabs, wherein the spacers in the second set of spacers each form at least one coinciding spacer aperture, wherein the coinciding spacer aperture is in alignment with the coincident alignment apertures in the second set of conductive tabs, wherein the coincident alignment apertures in the first set of conductive tabs are orientated differently than the coincident alignment apertures in the second set of conductive tabs to prevent interchanging electrode elements of the first set of electrode elements with electrode elements of the second set of electrode elements within the electrode stack during assembly of the electrode stack, and
wherein the spacers in the first set of spacers are interchangeable with the spacers in the second set of spacers for assembly of the electrode stack; and
a feedthrough including a feedthrough pin extending through the battery case, wherein the feedthrough pin is electrically coupled to the first set of conductive tabs and serves as a terminal for the battery.
2. The battery of claim 1, wherein the feedthrough pin extends through at least one of the alignment apertures in the first set to electrically couple the feedthrough pin to the first set of electrode elements.
3. The battery of claim 2, wherein the feedthrough is a first feedthrough and the feedthrough pin is a first feedthrough pin, the battery further comprising:
a second feedthrough including a second feedthrough pin extending through the battery case and through at least one of the alignment apertures in the second set to electrically couple the second feedthrough pin to the second set of electrode elements,
wherein the first feedthrough pin serves as a positive terminal for the battery, and
wherein the second feedthrough pin serves as a negative terminal for the battery.
4. The battery of claim 3, further comprising:
a first set of one or more spacers, wherein the spacers in the first set are positioned between each adjacent tab of the first set of conductive tabs, wherein the spacers in the first set of spacers each form at least one coinciding spacer aperture, wherein the coinciding spacer aperture is in alignment with the coincident alignment apertures in the first set of conductive tabs, wherein the first feedthrough pin also extends through at least one coinciding spacer aperture in each of the spacers in the first set of spacers; and a second set of one or more spacers, wherein the spacers in the second set are positioned between each adjacent tab of the second set of conductive tabs, wherein the spacers in the second set of spacers each form at least one coinciding spacer aperture, wherein the coinciding spacer aperture is in alignment with the coincident alignment apertures in the second set of conductive tabs, wherein the second feedthrough pin also extends through at least one coinciding spacer aperture in each of the spacers in the second set of spacers.

5. The battery of claim 1 further comprising an electrically conductive jumper in physical contact with at least one conductive tab of the first set of conductive tabs and with the feedthrough pin to electrically couple the feedthrough pin to the first set of electrode elements, wherein the jumper includes at least one jumper alignment aperture, wherein the jumper alignment aperture is coincident with the alignment apertures in the first set, wherein the jumper alignment aperture is configured to restrict rotation of the jumper and locate the jumper relative to the electrode stack when the jumper alignment aperture is positioned over the first set of one or more mating alignment protrusions.

6. The battery of claim 5, wherein the feedthrough further includes a ferrule sealed to the case and an insulator separating the ferrule from the feedthrough pin, wherein a majority of the ferrule is located within the enclosure.

7. The battery of claim 5, wherein the feedthrough further includes a ferrule sealed to the case and an insulator separating the ferrule from the feedthrough pin, wherein a majority of the ferrule is located outside the enclosure, wherein the battery case provides a thickness along as measured along the shortest dimension of the battery case, wherein a longitudinal axis of the feedthrough is about parallel the shortest dimension of the battery case, and wherein the feedthrough does not extend beyond the thickness of the battery case.

8. The battery of claim 5, wherein the second set of conductive tabs is electrically coupled to the battery case.

9. The battery of claim 1, further comprising:

a first weld joint connecting each of the first set of conductive tabs to each other and to the first set of one or more spacers; and a second weld joint connecting each of the second set of conductive tabs to each other and to the second set of one or more spacers.

10. The battery of claim 1, wherein the alignment apertures in the first set comprise two round holes, and wherein the alignment apertures in the second set also comprise two round holes.

11. The battery of claim 10, wherein the round holes of the alignment apertures in the first set and the second set each has a diameter of no greater than about 0.010 inches.

12. The battery of claim 1, wherein the second set of conductive tabs is electrically coupled to the battery case.

13. The battery of claim 1, wherein each of the first set of electrode elements and the second set of electrode elements comprises:

a conductive current collector with one of the first set of conductive tabs extending from the current collector, wherein the one of the first set of conductive tabs extending from the current collector is substantially coplanar with the current collector; and an electrode material disposed over the current collector.

14. The battery of claim 1, further comprising one or more separators positioned between each pair of adjacent electrode elements in the first and second set of electrode elements.

15. The battery of claim 1, wherein the feedthrough pin has a diameter of no greater than about 0.030 inches.

16. The battery of claim 1, wherein the alignment apertures in the first set include at least three alignment apertures and wherein the alignment apertures in the second set include at least three alignment apertures.

17. A battery comprising:

a battery case forming a substantially sealed enclosure;

an electrode stack within the enclosure, the electrode stack including a first set of plate electrodes and a second set of plate electrodes, the plate electrodes in the second set alternating with the plate electrodes in the first set within the electrode stack, wherein the plate electrodes in the first and second sets of plate electrodes each includes a conductive substrate serving as a current collector, and an electrode material disposed over the current collector, wherein the conductive substrate includes a conductive tab that does have the electrode material coating, wherein the electrode stack includes a first set of one or more spacers that are positioned between each adjacent tab of the conductive tabs in the first set of plate electrodes, wherein the electrode stack further includes a second set of one or more spacers that are positioned between each adjacent tab of the in the second set of plate electrodes;

wherein the conductive tabs in the first set of plate electrodes and the first set of spacers are aligned to form a first set of at least two coincident alignment apertures that extends through the first set of plate electrodes and the first set of spacers, wherein the first coincident alignment aperture is configured to restrict rotation of the plate electrodes in the first set of plate electrodes to align the plate electrodes in the first set with each other when the conductive tabs in the first set of plate electrodes are positioned over a first set of one or more mating alignment protrusions during assembly of the electrode stack, wherein the conductive tabs in the second set of plate electrodes and the second set of spacers are aligned to form a second set of at least two coincident alignment apertures that extends through the second set of plate electrodes and the second set of spacers, wherein the second set of at least two coincident alignment apertures is configured to restrict rotation of the plate electrodes in the second set of plate electrodes to align the plate electrodes in the second set with each other when the conductive tabs in the second set of plate electrodes are positioned over a second set of one or more mating alignment protrusions during assembly of the electrode stack, wherein the coincident alignment apertures in the first set of conductive tabs are orientated differently than the coincident alignment apertures in the second set of conductive tabs to prevent interchanging electrode elements of the first set of electrode elements with electrode elements of the second set of electrode elements within the electrode stack during assembly of the electrode stack, and wherein the spacers in the first set of spacers are interchangeable with the spacers in the second set of spacers for assembly of the electrode stack;

a feedthrough including a feedthrough pin extending through the battery case, wherein the feedthrough pin is electrically coupled to the first set of conductive tabs and serves as a positive terminal for the battery; and an electrically conductive jumper in electrical contact with at least one of the first set of conductive tabs and with the feedthrough pin to electrically couple the feedthrough pin to the first set of electrode elements, wherein the jumper includes at least one jumper alignment aperture, wherein the jumper alignment aperture is coincident with the alignment apertures in the first set, wherein the jumper alignment aperture is configured to restrict rotation of the jumper and locate the jumper relative to the electrode stack when the jumper alignment aperture is positioned over the first set of one or more mating alignment protrusions during assembly of the electrode stack, wherein the feedthrough further includes a ferrule sealed to the case and an insulator separating the ferrule from the feedthrough pin, wherein a majority of the ferrule is located within the enclosure.

18. The battery of claim 17, wherein the feedthrough extends through a substantially flat cover of the battery case.

19. The battery of claim 17, wherein the first set of plate electrodes combine with the second set of plate electrodes to form at least one voltaic cell, the first set of plate electrodes forming a cathode of the voltaic cell and the second set of plate electrodes forming an anode of the voltaic cell.

20. A battery comprising:

a battery case forming a substantially sealed enclosure;

an electrode stack within the enclosure, the electrode stack including a first set of plate electrodes and a second set of plate electrodes, the plate electrodes in the second set alternating with the plate electrodes in the first set within the electrode stack, wherein the plate electrodes in the first and second sets of plate electrodes each includes a conductive substrate serving as a current collector, and an electrode material disposed over the current collector, wherein the conductive substrate includes a conductive tab that does have the electrode material coating, wherein the electrode stack includes a first set of one or more spacers are positioned between each adjacent tab of the conductive tabs in the first set of plate electrodes, wherein the electrode stack further includes a second set of one or more spacers are positioned between each adjacent tab of the in the second set of plate electrodes;

wherein the conductive tabs in the first set of plate electrodes and the first set of spacers are aligned to form a first set of at least two coincident alignment apertures that extends through the first set of plate electrodes and the first set of spacers, wherein the first set of at least two coincident alignment apertures is configured to restrict rotation of the plate electrodes in the first set of plate electrodes to align the plate electrodes in the first set with each other when the conductive tabs in the first set of plate electrodes are positioned over a first set of one or more mating alignment protrusions during assembly of the electrode stack, wherein the conductive tabs in the second set of plate electrodes and the second set of spacers are aligned to form a second set of at least two coincident alignment apertures that extends through the second set of plate electrodes and the second set of spacers, wherein the second coincident set of at least two alignment apertures is configured to restrict rotation of the plate electrodes in the second set of plate electrodes to align the plate electrodes in the second set with each other when the conductive tabs in the second set of plate electrodes are positioned over a second set of one or more mating alignment protrusions during assembly of the electrode stack wherein the coincident alignment apertures in the first set of conductive tabs are orientated differently than the coincident alignment apertures in the second set of conductive tabs to prevent interchanging electrode elements of the first set of electrode elements with electrode elements of the second set of electrode elements within the electrode stack during assembly of the electrode stack, and wherein the spacers in the first set of spacers are interchangeable with the spacers in the second set of spacers for assembly of the electrode stack;

a feedthrough including a feedthrough pin extending through the battery case, wherein the feedthrough pin is electrically coupled to the first set of conductive tabs and serves as a positive terminal for the battery; and an electrically conductive jumper in physical contact with at least one of the first set of conductive tabs and with the feedthrough pin to electrically couple the feedthrough pin to the first set of electrode elements, wherein the jumper includes at least one jumper alignment aperture, wherein the jumper alignment aperture is coincident with the alignment apertures in the first set, wherein the jumper alignment aperture is configured to restrict rotation of the jumper and locate the jumper relative to the electrode stack when the jumper alignment aperture is positioned over the first set of one or more mating alignment protrusions during assembly of the electrode stack, wherein the feedthrough further includes a ferrule sealed to the case and an insulator separating the ferrule from the feedthrough pin, wherein a majority of the ferrule is located outside the enclosure, wherein the battery case provides a thickness measured along the shortest dimension of the battery case, wherein the feedthrough is parallel the shortest dimension of the battery case, and wherein the feedthrough does not extend beyond the thickness of the battery case.

21. The battery of claim 20, wherein the first set of plate electrodes combine with the second set of plate electrodes to form at least one voltaic cell, the first set of plate electrodes forming a cathode of the voltaic cell and the second set of plate electrodes forming an anode of the voltaic cell.

* * * * *